United States Patent
Webb

(10) Patent No.: US 9,808,608 B2
(45) Date of Patent: Nov. 7, 2017

(54) HELICAL COIL DELIVERY DEVICE FOR ACTIVE AGENT

(71) Applicant: International Business Machines Corporation, Armonk, NY (US)

(72) Inventor: Bucknell C. Webb, Yorktown Heights, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

(21) Appl. No.: 14/542,614

(22) Filed: Nov. 16, 2014

(65) Prior Publication Data

US 2016/0136401 A1    May 19, 2016

(51) Int. Cl.
*A61K 9/22* (2006.01)
*A61M 31/00* (2006.01)

(52) U.S. Cl.
CPC .................. *A61M 31/002* (2013.01)

(58) Field of Classification Search
CPC .................................. A61M 31/002
USPC ...................................... 604/890.1
See application file for complete search history.

(56) References Cited

U.S. PATENT DOCUMENTS

| | | | |
|---|---|---|---|
| 3,625,214 A | 12/1971 | Higuchi | |
| 5,500,013 A | 3/1996 | Buscemi | |
| 6,652,581 B1 | 11/2003 | Ding | |
| 7,473,248 B2 | 1/2009 | Santini, Jr. | |
| 7,510,551 B2 | 3/2009 | Uhland | |
| 7,806,925 B2 | 10/2010 | Buscemi | |
| 7,901,397 B2 | 3/2011 | Santini, Jr. | |
| 7,910,151 B2 | 3/2011 | Uhland | |
| 8,211,092 B2 | 7/2012 | Uhland | |
| 8,308,794 B2 | 11/2012 | Martinson | |
| 8,784,475 B2 | 7/2014 | Martinson | |
| 2007/0191816 A1* | 8/2007 | Behan | A61F 2/88 604/890.1 |
| 2010/0110372 A1 | 5/2010 | Pugh | |
| 2012/0162600 A1 | 6/2012 | Pugh | |
| 2012/0236524 A1 | 9/2012 | Pugh | |

FOREIGN PATENT DOCUMENTS

| | | |
|---|---|---|
| CN | 1331580 A | 1/2002 |
| CN | 1377258 A | 10/2002 |
| CN | 1681542 A | 10/2005 |
| CN | 101460213 A | 6/2009 |
| JP | 2006061383 A | 3/2006 |

OTHER PUBLICATIONS

Authorized Officer Jing Li, State IP Office of the P.R. China as ISA, International Search Report, PCT Application PCT/IB2015/058310, p. 1-5, dated Mar. 16, 2016.
Authorized Officer Jing Li, State IP Office of the P.R. China as ISA, Written Opinion of the ISA, PCT Application PCT/IB2015/058310, p. 1-4, dated Mar. 11, 2016.

* cited by examiner

*Primary Examiner* — Kevin C Sirmons
*Assistant Examiner* — Deanna K Hall
(74) *Attorney, Agent, or Firm* — Louis J. Percello; Otterstedt, Ellenbogen & Kammer, LLP

(57) ABSTRACT

A delivery device including a substrate formed in a coil comprising a plurality of loops, an active agent deposited between an inner surface and an outer surface of the substrate formed in the coil, and a pair of end caps, each end cap disposed on a corresponding end of the coil.

10 Claims, 9 Drawing Sheets

HELICAL COIL DELIVERY DEVICE FOR ACTIVE AGENT

BACKGROUND

The present disclosure relates to a delivery device for an active agent, and more particularly to a delivery device having a form of a helical coil.

Integrated delivery devices that use silicon electronics to trigger a timed release of units of medication rely on cavities etched into silicon with ruptureable membranes.

BRIEF SUMMARY

According to an exemplary embodiment of the present invention, a delivery device including a substrate formed in a coil comprising a plurality of loops, an active agent deposited between an inner surface and an outer surface of the substrate formed in the coil, and a pair of end caps, each end cap disposed on a corresponding end of the coil.

According to one or more embodiments of the present invention, a delivery device comprises a substrate formed in a coil, a plurality of cavities disposed along a length of the substrate between an inner surface and an outer surface of the substrate formed in the coil, and a plurality of seals defining a closed volume of the cavities, wherein the seals are configured for sequential opening of the cavities.

BRIEF DESCRIPTION OF THE SEVERAL VIEWS OF THE DRAWINGS

Preferred embodiments of the present invention will be described below in more detail, with reference to the accompanying drawings.

DETAILED DESCRIPTION

Figure 1:
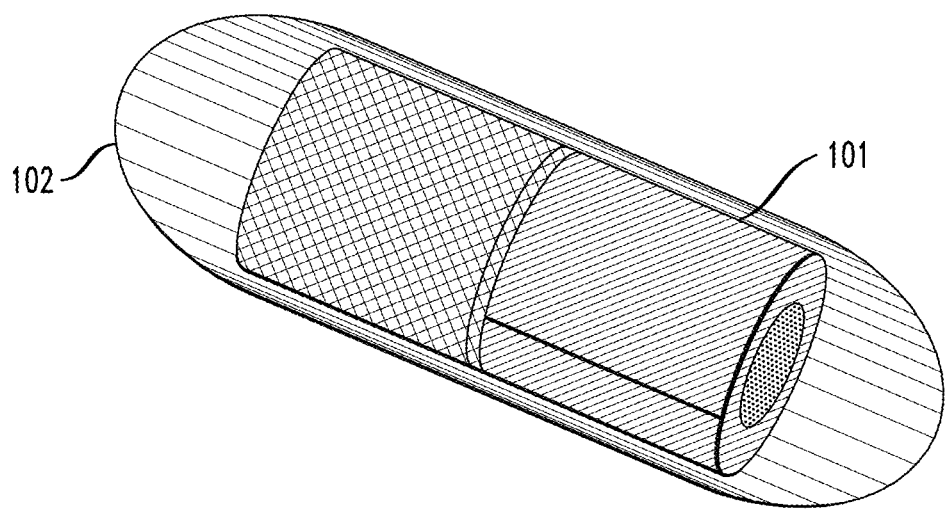
FIG. 1 is a helical coil delivery device according to an exemplary embodiment of the present invention.

According to an exemplary embodiment of the present invention, a helical coil 101 of patterned polymer is configured for delivery of an active agent, such as medication, a therapeutic agent, a solution, etc. (see FIG. 1). The helical coil can be formed of patterned polymer (e.g., KAPTON), wherein the patterned polymer forms a plurality of cavities. The helical coil 101 can be disposed in a capsule 102. According to one or more embodiments of the present invention, the helical coil is configured to open in a controlled way, wherein the cavities are sequentially opened. For example, the helical coil includes a dissolvable hydrogel, which opens the helical coil is a sequential manner, or a power source and electrical conductors connected to heaters, which control the opening or unrolling of the helical coil, wherein the opening thereby releases the contents of the cavities in a controlled way.

It should be understood that a delivery device according to exemplary embodiments of the present invention can be ingestible, implantable, injectable, etc.

According to one or more embodiments of the present invention, the helical coil (200, FIG. 2) is formed of a substrate 201 (e.g., polymer) including a plurality of cavities, e.g., 202, and an integrated battery or secondary winding 203. In the case of a secondary winding 203, a wireless power transmission (e.g., primary winding) device external to the delivery device can be used as a power supply. Each cavity is surrounded by one or more seal structures (see 204, see also FIG. 3, which is a view along section AA in FIG. 2), which are configured to seal the cavities 202. One or more heating elements 301 are disposed in an insulator 302 below each seal structure 204 (e.g., indium solder structures), and are connected to the battery 203 by wiring 205. The seal structures 204 can be a metal, a solder, etc., having a melting point sufficiently low to be melted by the heating elements 301. The heating elements 301 can be formed of, for example, Cu, CuNi, Ti, TiCu, Al, etc. A cavity liner 303 can be formed over the insulator 302. The cavity liner 303 can be formed of, for example, Ti, Au, Al, Parylene, wax, etc.

In one or more embodiments, the heating element 301, powered by the battery 203, opens the seal structure 204 for controlled opening of the helical coil 200. The helical coil structure can be made with planar integrated wafer/sheet or roll processes, wherein the substrate 201 is formed on a solder bond material 206 (e.g., Cu/Au or Cu/Ni/Cu/Au) for joining the helical coil to itself in a rolled configuration.

Figure 6:
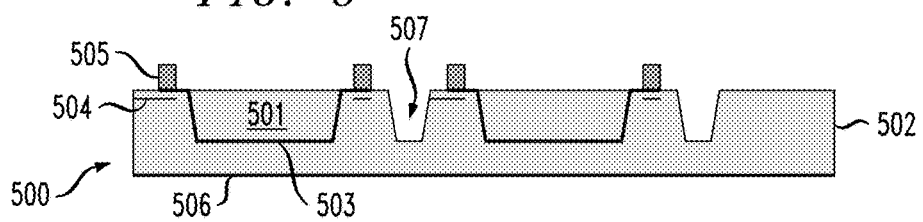

According to one or more embodiments of the present invention, each cavity 202 has a volume defined by a depth, length and width in the polymer and the cavities are separated by flex joints (see FIG. 6, 507). The volume of a cavity can be controlled during manufacture, e.g., for shape requirements. As the cavity depth approaches the thickness of the polymer, the fraction of the total volume allotted to the cavities can be large.

Figure 2:
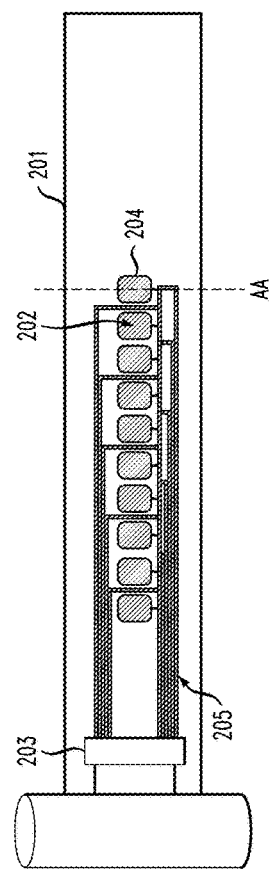
FIG. 2 is an uncoiled delivery device according to an exemplary embodiment of the present invention.
Figure 4:
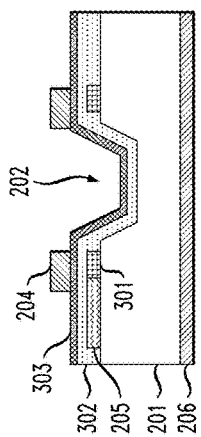
FIG. 4 is a cross section of a delivery device according to an exemplary embodiment of the present invention.

FIG. 4 shows a section along AA in FIG. 2 and further includes a release material 401, such as an organic material, Parylene, wax, plastic, etc. formed between the insulator 302 and the seal structure 204.

Figure 3:
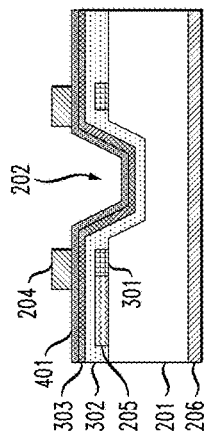
FIG. 3 is a cross section of a delivery device according to an exemplary embodiment of the present invention.

With reference to FIG. 3 and hereinafter, a surface 304 including the cavities is referred to as an inner surface and a surface 305 formed by the solder bond material 206 is referred to as an outer surface. That is, inner and outer refer to an arrangement of the surfaces in a helical coil, e.g., the inner surfaces faces inward.

Figure 5:
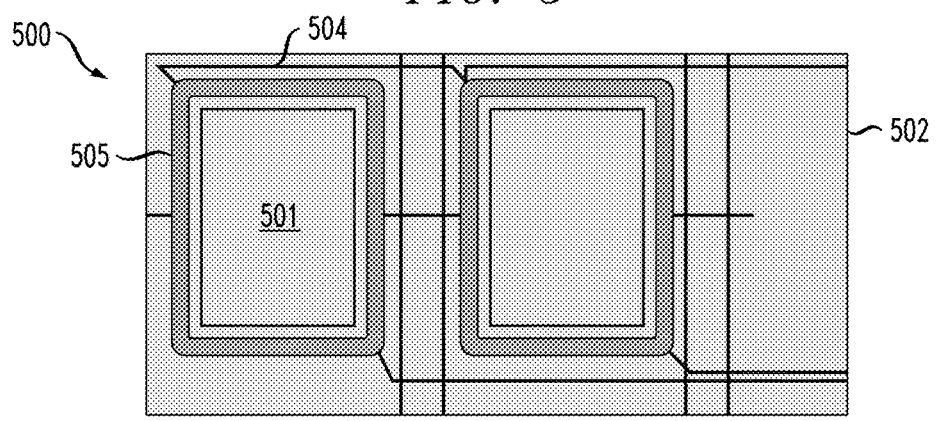
FIG. 5 and FIG. 6 are diagrams of a helical coil delivery device according to an exemplary embodiment of the present invention.

FIG. 5 and FIG. 6 show top and sectional views of a helical coil 500 according to an embodiment of the present invention. Cavities 501 are etched in a substrate 502 (e.g., polyimide) and lined with a metal liner 503. Resistive connections 504, including heating elements and wiring, are formed below the solder structures 505 and can be shorted by the solder bond material 506, which serves as a solder connection sense. For connection sensing, an electrical path is established on a first surface that uses a solder connection to an electrical pad on the other surface to complete the electrical path. When the surfaces separate and the pad moves away from the first surface the electrical path is broken, signaling the opening of the neighboring cavity. Flex joints 507 can be formed in the substrate to aid in rolling the helical coil 500.

Figure 7:
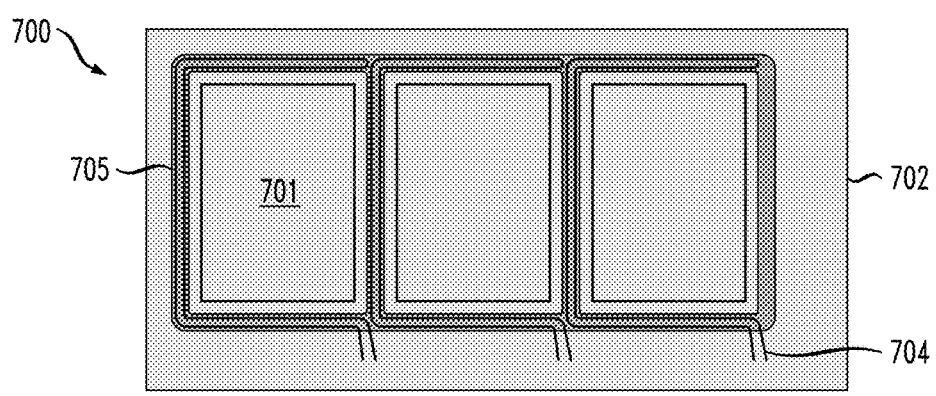
FIG. 7 and FIG. 8 are diagrams of a helical coil delivery device according to an exemplary embodiment of the present invention.
Figure 8:
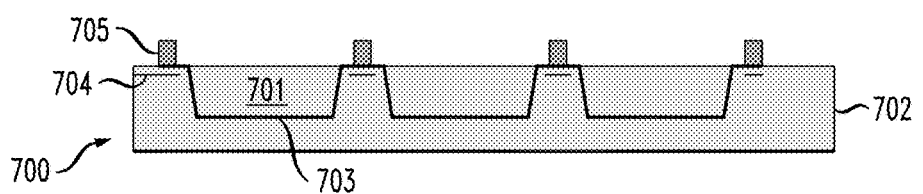

FIG. 7 and FIG. 8 show top and sectional views of a helical coil 700 according to an embodiment of the present invention. Cavities 701 are etched in a substrate 702 (e.g., polyimide) and lined with a metal liner 703. Resistive connections 704, including heating elements and wiring, are formed below the solder structures 705. The cavities can then be chained, wherein buried heating elements 704 are folded back on themselves in a configuration wherein the heating elements are turned on in pairs to open a next cavity. The pair of heating elements includes one used in opening a prior cavity and one used for a current opening.

Figure 9:
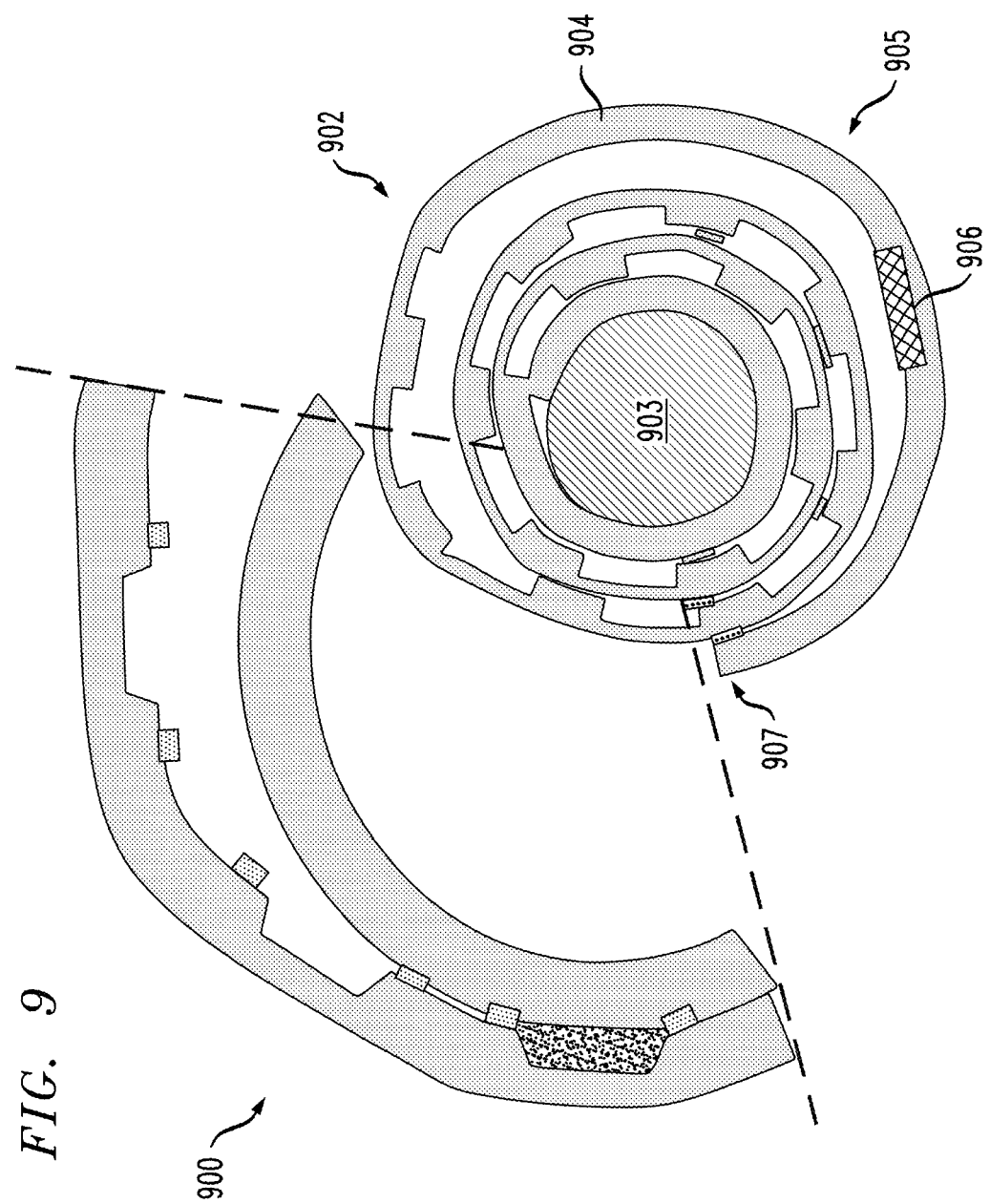
FIG. 9 is sectional view of a helical coil delivery device according to an exemplary embodiment of the present invention.

According to an exemplary embodiment of the present invention, FIG. 9 shows an expanded view of a portion 901 of a helical coil 902. The helical coil 902 includes a battery 903 integrated as part of a polymer coil 904. Over time, solder structures are opened (e.g., be melting), uncoiling the helical coil 902 and opening cavities sequentially. When included, flex joints (see FIG. 6, 507) promote the opening of the cavities. Flex joints enable the cavities to open fully, even when the outer portions of the helix are confined within a limiting outer radius by an outer container (e.g., see FIG. 1, 102) or where an outer diameter is fixed by a terminal connection 907. The helical coil 902 can have an outer loosely wrapped turn 905 with no cavities to hold a processor 906 and restrict maximum outer diameter. More particular, a terminal end 907 of the polymer coil 904 can be permanently fixed to the next inner turn. In this embodiment, the helical coil 902 uncoils within the outer loosely wrapped turn 905, such that the active agent exits the helical coil 902 in the axial direction.

Figure 10:
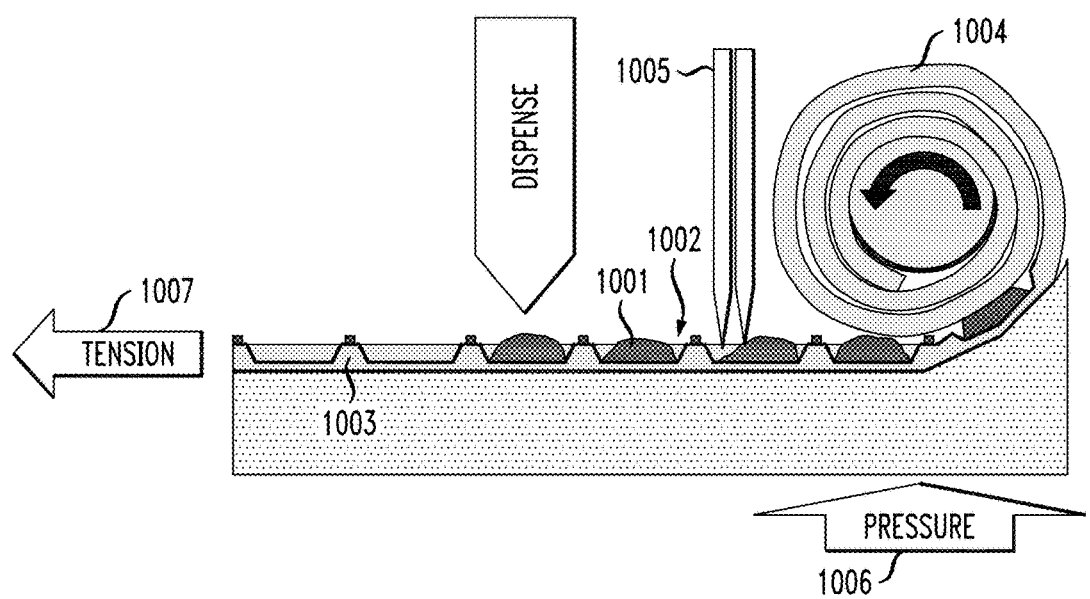
FIG. 10 illustrates a method of forming a helical coil delivery device according to an exemplary embodiment of the present invention.

In one or more embodiments, an active agent 1001 is dispensed into the cavities, e.g., 1002, while the substrate 1003 is disposed flat (see FIG. 10). The helical coil 1004 is gradually formed and held by sequential seals (e.g., solder structures). The solder structures can be sealed to the solder bond material below the substrate using magnetic induction heating, radio frequency (RF) heating, a surface heater 1005, a release heater and the like. During coiling, pressure 1006 can be applied to newly formed portions of the helical coil, while tension 1007 is maintained along a lateral direction of the substrate.

According to an exemplary embodiment of the present invention, RF heating can be used to melt solder structures formed in a closed electrical path. In such embodiments, each cavity is formed with a corresponding separate solder loops. Such solder structures can be melted and sealed to the solder bond material. More particularly, a coil generating an oscillating RF magnetic field or a rotating magnetic RF field loop pickup can be used to achieve inductive heating. For example, in FIG. 11, a first and second pair of RF coils (A and B) are disposed around a helical coil 1101 having cavities with a separate solder loops for each cavity. The first and second pair of RF coils emit out-of-phase oscillator signals. The first pair of coils (A) applies a signal sin(wt) and a second pair of coils (B) applies a signal cos(wt), where w is frequency and t is time. The solder can be melted when a current is induced in the solder flowing around the closed electrical path. In one or more embodiments, an outer turn of the helical coil is positioned to create an outer cylinder, which is glued or soldered in place. The outer cylinder is loose, allowing inner turns of the helical coil to open within the outer cylinder.

In one or more embodiments, the substrate is immersed in an active agent and the helical coil formed therein to fill the cavities.

Figure 11:
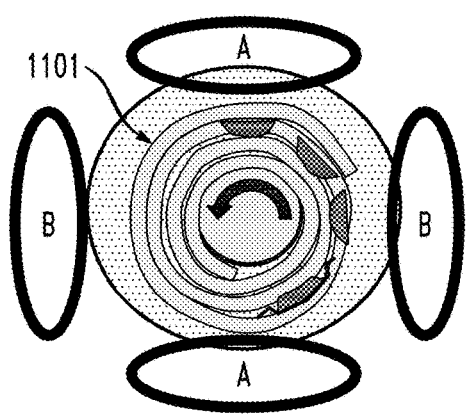
FIG. 11 illustrates a method of forming a helical coil delivery device according to an exemplary embodiment of the present invention.
Figure 12:
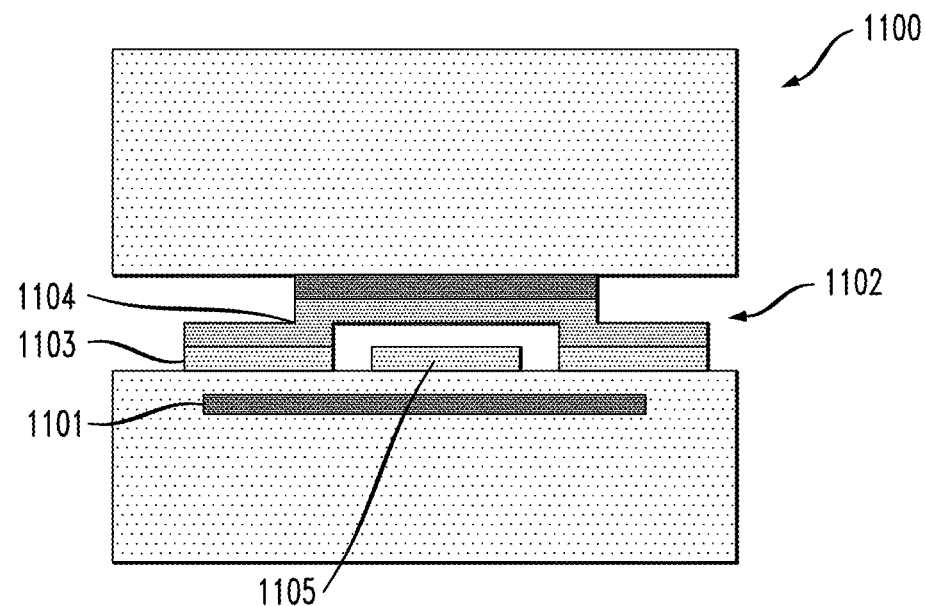
FIG. 12 is a diagram of a single use switches according to an exemplary embodiment of the present invention.
Figure 13:
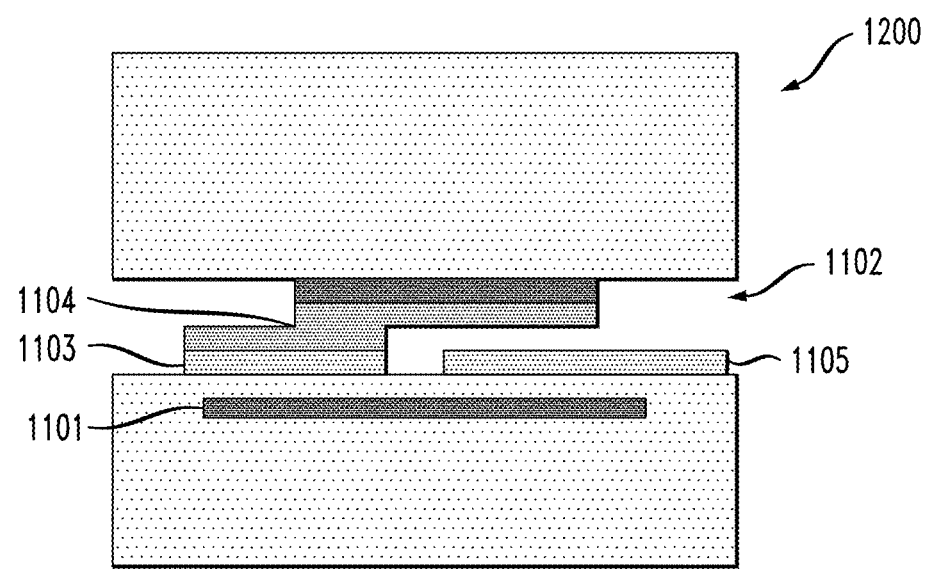
FIG. 13 is a diagram of a single use switches according to an exemplary embodiment of the present invention.

FIG. 11 and FIG. 12 are exemplary embodiments of one-time switches 1100 and 1200. A heating element 1101 is disposed below a switch 1102. A source (Vin) 1103 is disposed in contact with solder 1104. A drain (Vout) 1105 is disposed separated from the solder 1104. A shorting contact 1106 (e.g., solder bond material) contacts the solder 1104. When the heating element receives a voltage on the source 1003, the solder 1104 collapses down, preferentially wetting drain 1105.

Figure 14:
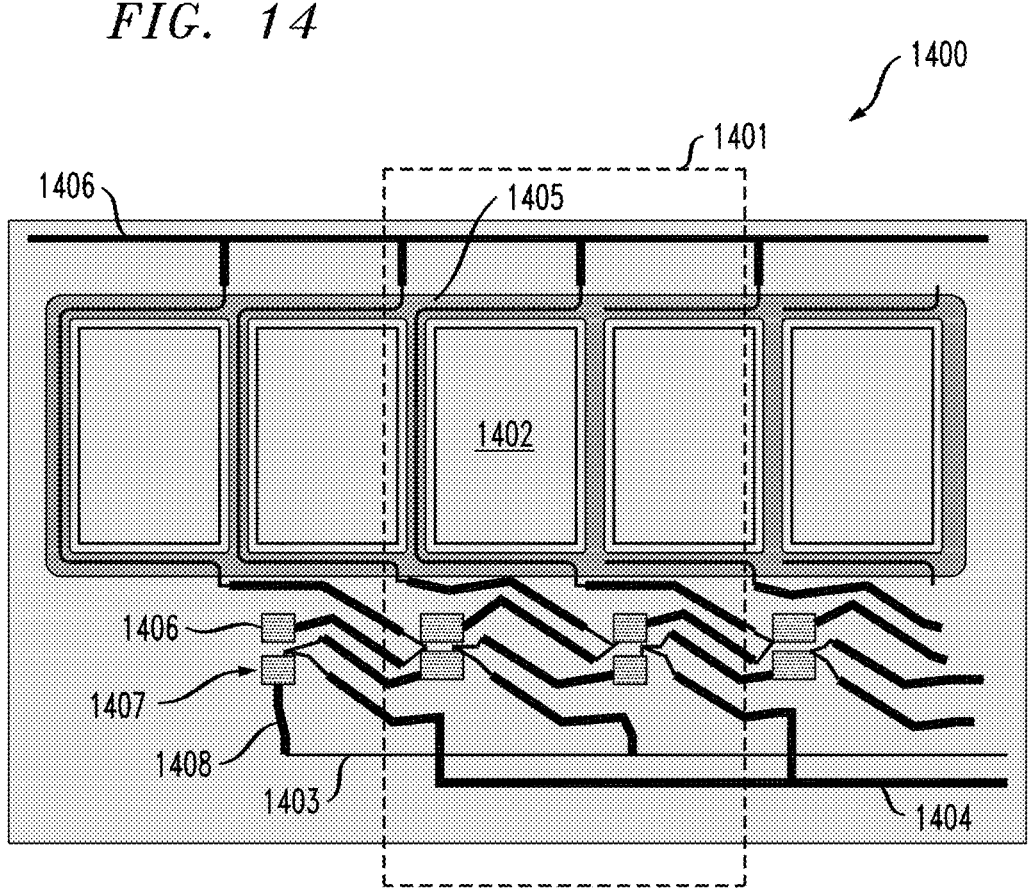
FIG. 14 is a diagram of a wiring layer of a delivery device according to an exemplary embodiment of the present invention.
Figure 14:
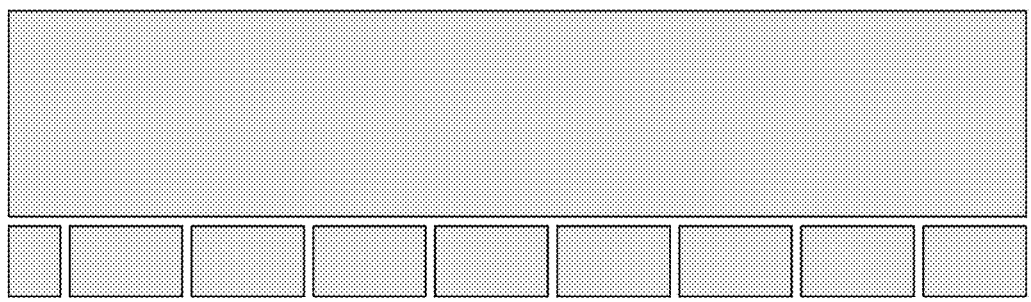

Referring now to FIG. 14 and exemplary wiring in a helical coil 1400, an area 1401 is repeated for multiple cavities, e.g., 1402. Heating element current supply lines 1403 and 1404 are connected to alternate successive heaters, e.g., 1405. A current return 1406 is connected to the heater elements 1405. Solder points 1407 (e.g., electrical pads) are connected to a wiring layer (e.g., 1408) in the one-time switch layout.

For n (bit) by m (word) line addressing, successive cavities step through bit lines. Every nth cavity is a new word line. For example, in a helical coil having 16 cavities, a 4 word by 4 bit wiring is needed.

In operation, sequential solder joints are melted turning on corresponding heating elements. For example, when a heating element is turned on, the melting solder wets to electrical pads on the inner surface of the helical coil (e.g., see FIG. 2, 206) and the outer surface of a next turn of the helical coil. Thus, the solder establishes a new continuous electrical path.

In a case of a turn of the helical coil where the solder seals have been melted and the coil has unwound to open the corresponding cavities, the electrical pads on the inner surface of the open turn and the outer surface of a next turn are separated with no electrical connection therebetween.

By combining these electrical path elements (e.g., solder, electrical pads formed on inner surfaces and the solder bond material formed on outer surfaces) an electrical switching network is constructed, which is controlled by a processor to time and control cavity opening.

According to an exemplary embodiment of the present invention, when a heating element is turned on, it closes a next solder switch. Resistance in an off heating element path increases and closes as the substrate forming a lid lifts and a next solder switch is actuated.

The electrical pads used to form and open connections in the electrical switching network are shaped and arranged to align with electrical pathways formed in the solder bond material. The arrangement of the electrical pads and the electrical pathways formed in the solder bond material obviates the need to enforce a specific diameter of each turn in the helical coil, such that each subsequent turn of the helical coil aligns circumferentially. FIG. 14 shows one such arrangement of these electrical pads 1407. Other arrangements are readily apparent, such as disposing the electrical pads 1407 at different positions along an axis of the helical coil.

Figure 15:
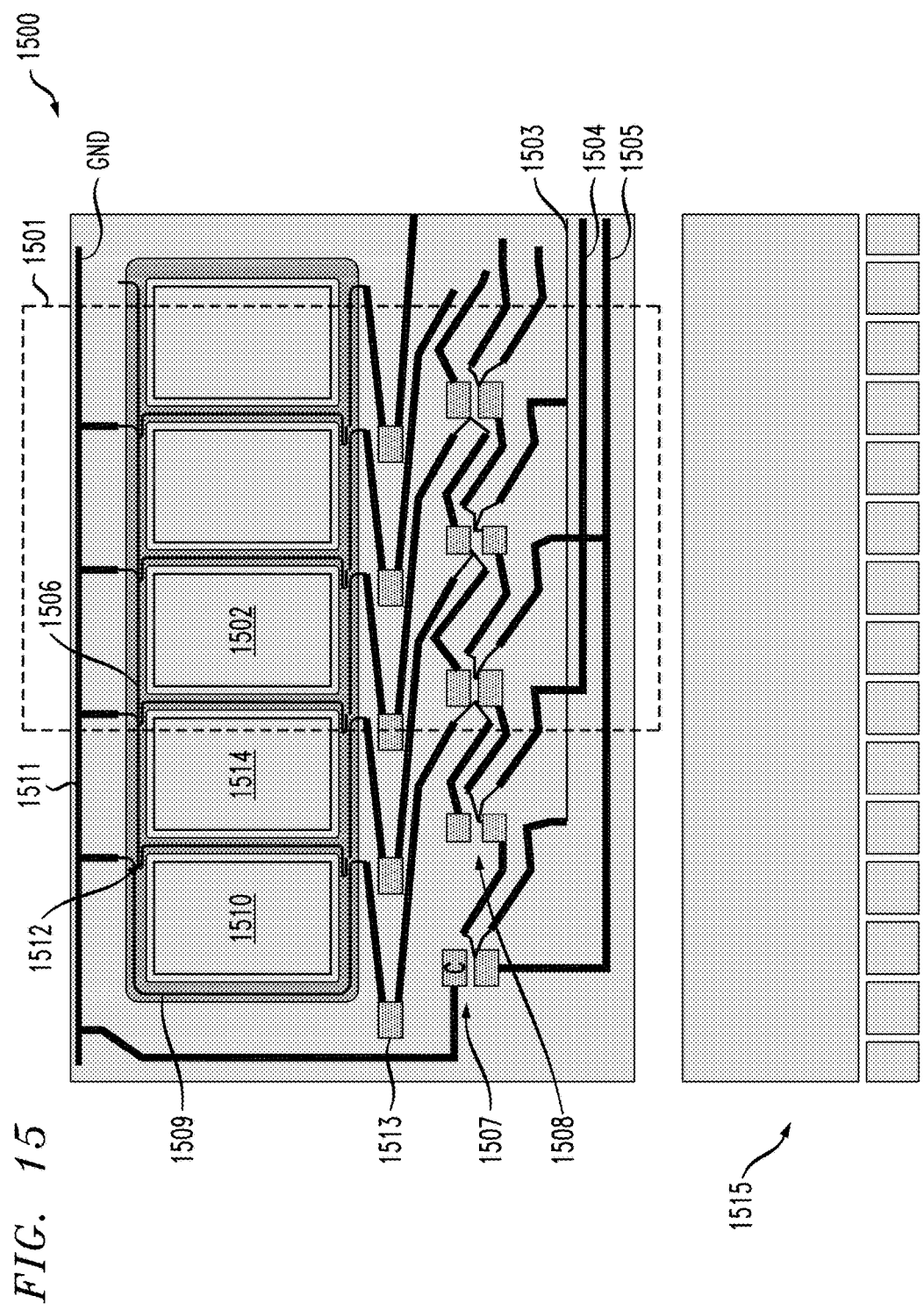
FIG. 15 is a diagram of a wiring layer of a delivery device according to an exemplary embodiment of the present invention.

Referring now to FIG. 15 and exemplary wiring in a helical coil 1500, an area 1501 is repeated for multiple cavities, e.g., 1502. Heating element current supply lines 1503, 1504 and 1505 are connected to successive heaters, e.g., 1506.

In operation, to open cavity 1510, switches 1507 and 1508 are closed or turned on by a solder connection to the solder bond material (e.g., backside or outer surface metal), and all other switches remain normal, with no connection between the electrical pads through the solder bond material. A line 1509 at the opening cavity 1510 is itself opened. The line 1511 is a ground (GND) line, which closes as the electrical pads and switch heats. An overlap jog 1512 in the heating element helps achieve full release of the previous cavity joint. A contact pad 1513 is disposed for an external probe contact to melt solder during helix formation.

When opening cavity 1514, i.e., after opening cavity 1510, switch 1707 is now open, with the solder bond material lifted away.

The patterning of the solder bond material or backside metal 1515 is configured such that there are no shorts between switches through the backside metal. As long as the gaps in the pattern are small compare to the switch area, inner surfaces and outer surfaces do not need to be aligned. Alignment of the inner surface and outer surface shifts by an amount about equal to 2pi*t for each complete loop. This shifting can be compensated for in the patterning of the solder bond material so that the electrical pads and solder bond material align.

Figure 16:
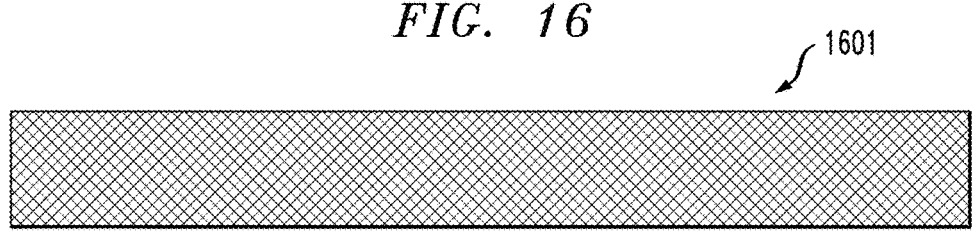
FIGS. 16-19 are diagrams of different passive helical coils according to one or more exemplary embodiments of the present invention.

According to an exemplary embodiment of the present invention, dissolving materials (e.g., hydrogels, cellulose derivative polymers, gelatin, gelatin/polyethylene glycol (PEG) and hydroxypropyl methylcellulose (HPMC)) are used within a passive helical coil. The passive helical coils are non-electric and in one or more embodiments lack the processors, wiring and heating elements of an active helical coil. In one or more embodiments the dissolving material includes the active agent, and is deposited on an entire inner surface of the substrate 1601 (see FIG. 16). In the example of FIG. 16, the substrate need not include cavities. In one or more embodiments, the dissolving materials define seals, e.g., 1701, between cavities, e.g., 1702, carrying the active agent, creating a periodic release of an amount of active agent according to a size of the cavity (see FIG. 17).

Figure 17:
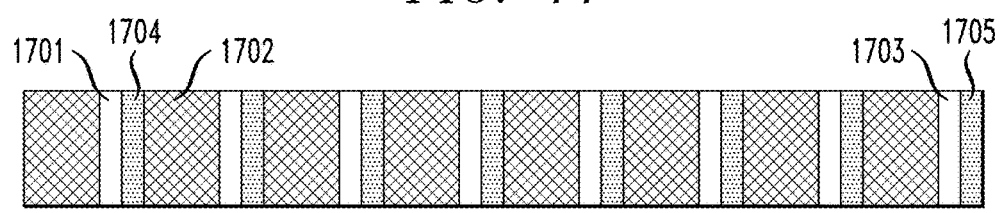
Figure 18:
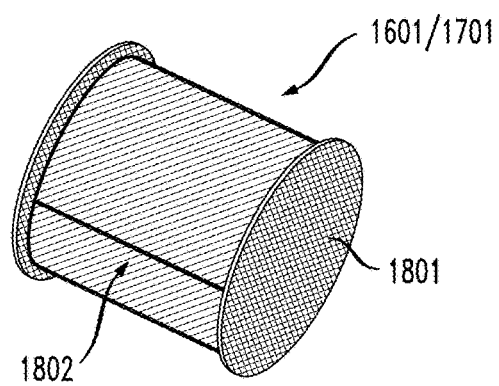

According to an exemplary embodiment of the present invention, ends of the helical coil can be capped to block ingress of fluid at the helix ends as shown in FIG. 18 (for example, in the embodiments shown in FIG. 16 and FIG. 17). In this example, the active agent diffuses out along a helical path of the helical coil. End caps 1801 can be a deposited film such as parylene, which is scribed or masked open at an exposed end 1802 of the helical roll to create the fluid entry path. No water/fluid reaches a cavity barrier until the previous cavity is open, the fluid follows the helical path to reach each seal region. In the example FIG. 17, a terminal seal structure 1703 can be formed at the exposed end 1802, sealing the helical path.

Figure 19:
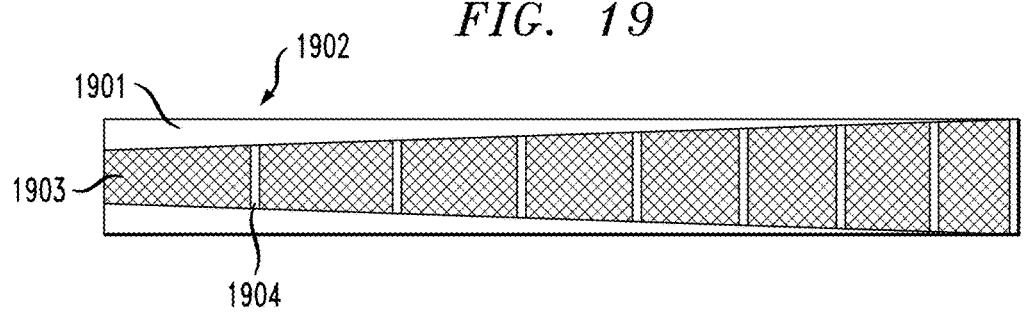

According to an exemplary embodiment of the present invention, first structures, e.g., 1901, formed of dissolving material are deposited at ends of the substrate along a length of the substrate 1902. The first structure 1901 has a variable thickness (e.g., increasing away from an exposed end of the helical coil). Cavities, e.g., 1903, along the length of the substrate 1902 are separated by second structures, e.g., 1904, formed of the dissolving material. In the example shown in FIG. 19, the volume of each cavity is equal (e.g., within a threshold for dosing the active agent), wherein the second structures are arraigned at variable distances from one another that compensate for the variable thickness of the first structures.

In one or more embodiments, the seal structures can include hard seals (e.g., 1701) and a swelling material (e.g., 1704) deposited along the hard seals. In this case, the swelling material portion of the seal structure breaks the hard seal portion of the seal structure and terminal seal structure successively as a liquid (e.g., water, blood, digestive fluid, etc.) gains admission further into the helical coil. In the case of the terminal seal structure 1703, a terminal swelling material 1705 is deposited along an outer surface of the seal structure (i.e., at the exposed end 1802 in FIG. 18).

By way of recapitulation, according to an exemplary embodiment of the present invention, a delivery device including a substrate formed in a coil comprising a plurality of loops, an active agent deposited between an inner surface and an outer surface of the substrate formed in the coil, and a pair of end caps, each end cap disposed on a corresponding end of the coil. According to one or more embodiments of the present invention, a delivery device comprises a substrate formed in a coil, a plurality of cavities disposed along a length of the substrate between an inner surface and an outer surface of the substrate formed in the coil, and a plurality of seals defining a closed volume of the cavities, wherein the seals are configured for sequential opening of the cavities.

The methodologies of embodiments of the disclosure may be particularly well-suited for use in an electronic device or alternative system. Accordingly, embodiments of the present invention may take the form of an entirely hardware embodiment or an embodiment combining software and hardware aspects that may all generally be referred to herein as a "processor," "circuit," "module" or "system."

The whole system shown in FIG. 2 is controlled by computer readable instructions, which are generally stored by the processor (e.g., see 906, FIG. 9).

The processor 906 may be configured to perform one or more methodologies described in the present disclosure, illustrative embodiments of which are shown in the above figures and described herein. Embodiments of the present invention can be implemented as a routine that is stored in memory and executed by the processor 906.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to the processor 906 to produce a machine, such that the instructions, which execute via the processor, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto the processor 906 to cause a series of operational steps to be performed to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Although illustrative embodiments of the present invention have been described herein with reference to the accompanying drawings, it is to be understood that the invention is not limited to those precise embodiments, and that various other changes and modifications may be made therein by one skilled in the art without departing from the scope of the appended claims.

The invention claimed is:

1. A delivery device comprising:
 a substrate rolled on itself to form a coil;
 an active agent deposited between an inner surface and an outer surface of the substrate formed in the coil, wherein the inner surface of the substrate at a first portion of the substrate contacts the outer surface of the substrate at a second portion of the substrate; and
 a pair of end caps, each end cap disposed on a corresponding end of the coil and along a respective exposed edge of the substrate.

2. The delivery device of claim 1, further comprising a terminal seal structure formed between the inner surface and the outer surface of the substrate formed in the coil disposed at an exposed end of the substrate.

3. The delivery device of claim 2, further comprising:
 a plurality of cavities disposed along a length of the substrate between the inner surface and the outer surface of the substrate formed in the coil; and
 a plurality of seal structures, including the terminal seal structure, defining volumes of the plurality of cavities, wherein the seals structures are configured for sequential opening of the plurality of cavities.

4. The delivery device of claim 3, wherein the structures are passive seals formed of a dissolving material.

5. The delivery device of claim 3, wherein the seal structures each comprise a hard seal portion and a swelling material portion.

6. The delivery device of claim 1, further comprising:
 a plurality of cavities disposed along a length of the substrate between the inner surface and the outer surface of the substrate formed in the coil; and
 a plurality of seal structures, including the terminal seal structure, defining first sides of the plurality of cavities, wherein the seals structures are configured for sequential opening of the cavities,
 wherein the pair of end caps define a second sides of the plurality of cavities, wherein the plurality of seal structures and the pair of end caps define a volume of the plurality of cavities.

7. The delivery device of claim 1, wherein the active agent is intermixed with a seal structure.

8. The delivery device of claim 1, further comprising:
 a plurality of first seal structures disposed along a length of the substrate between the inner surface and the outer surface of the substrate formed in the coil and defining a width of a plurality of cavities and having an increasing thickness away from an exposed end of the coil; and
 a plurality of second seal structures disposed along a length of the substrate between the inner surface and the outer surface of the substrate formed in the coil and defining a length of a plurality of cavities.

9. The delivery device of claim 3, further comprising a plurality of flex joints disposed in the substrate, wherein the plurality of flex joints and the cavities are alternately disposed and one of the flex joints is disposed between respective pairs of the cavities.

10. The delivery device of claim 1, wherein the first portion of the substrate is a distal portion relative to a center of the coil and the second portion of the substrate is a proximal portion relative to the center of the coil.

* * * * *